(12) United States Patent
Lesch, Jr.

(10) Patent No.: US 8,562,564 B2
(45) Date of Patent: *Oct. 22, 2013

(54) PREFILLED SYRINGE JET INJECTOR

(75) Inventor: Paul R. Lesch, Jr., Lino Lakes, MN (US)

(73) Assignee: Antares Pharma, Inc., Ewing, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/236,120

(22) Filed: Sep. 19, 2011

(65) Prior Publication Data

US 2012/0004608 A1 Jan. 5, 2012

Related U.S. Application Data

(63) Continuation of application No. 11/781,832, filed on Jul. 23, 2007, which is a continuation of application No. PCT/US2006/002429, filed on Jan. 24, 2006, now Pat. No. 8,021,335.

(60) Provisional application No. 60/645,590, filed on Jan. 24, 2005, provisional application No. 60/709,116, filed on Aug. 18, 2005.

(51) Int. Cl.
*A61M 5/20* (2006.01)
*A61M 5/32* (2006.01)
*A61M 5/315* (2006.01)

(52) U.S. Cl.
USPC .............................. 604/135; 604/218; 604/192

(58) Field of Classification Search
USPC ....................... 604/68–72, 181–243, 134–136
See application file for complete search history.

(56) References Cited

U.S. PATENT DOCUMENTS

| | | | |
|---|---|---|---|
| 4,378,015 A | 3/1983 | Wardlaw | 128/218 |
| 4,553,962 A | 11/1985 | Brunet | 604/198 |
| 4,790,824 A | 12/1988 | Morrow et al. | 604/143 |
| 5,062,830 A | 11/1991 | Dunlap | 604/68 |
| 5,104,380 A | 4/1992 | Holman et al. | 604/117 |
| 5,300,030 A | 4/1994 | Crossman et al. | 604/136 |
| 5,599,302 A | 2/1997 | Lilley et al. | 604/68 |
| 5,599,309 A | 2/1997 | Marshall et al. | 604/136 |
| 5,928,205 A | 7/1999 | Marshall | 604/263 |

(Continued)

FOREIGN PATENT DOCUMENTS

| | | | |
|---|---|---|---|
| EP | 0 518 416 | 12/1992 | ......... 5/20 |
| EP | 0518416 | 12/1992 | |

(Continued)

OTHER PUBLICATIONS

Japanese Office Action issued on Apr. 9, 2011 for Japanese Patent Application No. 2007-552367.

*Primary Examiner* — Nicholas Lucchesi
*Assistant Examiner* — Pritesh Patel
(74) *Attorney, Agent, or Firm* — Morgan, Lewis & Bockius LLP

(57) ABSTRACT

A jet injector that includes a prefilled syringe. The syringe includes a fluid chamber that contains a medicament. The syringe also has an injection-assisting needle, and a plunger is movable within the fluid chamber. A housing is configured for allowing insertion of the needle to a penetration depth. An energy source is configured for biasing the plunger to produce an injecting pressure in the medicament in the fluid chamber of between about 80 and 1000 p.s.i. to jet inject the medicament from the fluid chamber through the needle to an injection site.

28 Claims, 8 Drawing Sheets

(56) References Cited

U.S. PATENT DOCUMENTS

| | | | |
|---|---|---|---|
| 6,056,716 A | 5/2000 | D'Antonio et al. | 604/68 |
| 6,077,247 A | 6/2000 | Marshall et al. | 604/156 |
| 6,099,504 A | 8/2000 | Gross et al. | 604/140 |
| 6,159,181 A | 12/2000 | Crossman et al. | 604/157 |
| 6,231,540 B1 | 5/2001 | Smedegaard | 604/68 |
| 6,391,003 B1 | 5/2002 | Lesch, Jr. | 604/110 |
| 6,544,234 B1 | 4/2003 | Gabriel | 604/207 |
| 6,589,210 B1 | 7/2003 | Rolfe | 604/157 |
| 6,932,793 B1 | 8/2005 | Marshall et al. | 604/135 |
| 7,066,907 B2 | 6/2006 | Crossman et al. | 604/110 |
| 7,449,012 B2 | 11/2008 | Young et al. | 604/192 |
| 7,635,348 B2 | 12/2009 | Raven et al. | 604/111 |
| 8,021,335 B2 * | 9/2011 | Lesch, Jr. | 604/135 |
| 2001/0049496 A1 | 12/2001 | Kirchhofer et al. | 604/154 |
| 2002/0045866 A1 | 4/2002 | Sadowski et al. | |
| 2004/0220524 A1 | 11/2004 | Sadowski et al. | 604/117 |
| 2005/0165360 A1 | 7/2005 | Stamp | 604/187 |
| 2005/0256499 A1 | 11/2005 | Pettis et al. | |

FOREIGN PATENT DOCUMENTS

| | | | |
|---|---|---|---|
| JP | 11-347121 | 12/1999 | |
| WO | WO 95/29720 | 11/1995 | 5/20 |
| WO | WO 97/14455 | 4/1997 | |
| WO | WO 97/41907 | 11/1997 | 5/20 |
| WO | WO 99/22790 | 5/1999 | 5/20 |
| WO | WO 00/24441 | 5/2000 | 5/20 |
| WO | WO 03/070296 | 8/2003 | |
| WO | WO 03/097133 | 11/2003 | 5/32 |
| WO | WO 2004/108194 | 12/2004 | 5/20 |
| WO | WO 2005/002653 | 1/2005 | 5/32 |

* cited by examiner

PREFILLED SYRINGE JET INJECTOR

CROSS REFERENCE TO RELATED APPLICATIONS

This application is a continuation application of U.S. application Ser. No. 11/781,832, filed on Jul. 23, 2007, which is a continuation of International Application No. PCT/US2006/002429, filed Jan. 24, 2006, which claims the benefit of U.S. Provisional Application Nos. 60/645,590, filed Jan. 24, 2005, and 60/709,116, filed Aug. 18, 2005, the content of each of which is expressly incorporated herein by reference thereto.

FIELD OF THE INVENTION

The present invention relates to a jet injector, and more particularly to a needle-assisted jet injector that uses a low jet injection pressure.

BACKGROUND OF THE PRESENT INVENTION

Examples of needle-free injectors are described in U.S. Pat. Nos. 5,599,302; 5,062,830; and 4,790,824. These traditional injectors administer medication as a fine, high velocity jet delivered under sufficient pressure to enable the jet to pass through the skin. The pressure used to deliver the medication is typically greater than approximately 4000 p.s.i. inside the compartment that contains the medicament in the injector. Benefits derived from such pressures, in addition to allowing injection without needles, include the speed of the injection, the dispersion of the injected medicament in the tissue and injection delivery without impact from the resistance by the tissue where the medicament is delivered.

Self-injectors or autoinjectors like the ones disclosed in U.S. Pat. Nos. 4,553,962 and 4,378,015 and PCT Publications WO 95/29720 and WO 97/14455 are constructed to inject medicament at a rate and in a manner similar to hand-operated hypodermic syringes. The self-injectors or autoinjectors have needles that are extended at the time of activation to penetrate the user's skin to deliver medicament through movement of the drug container and related needle. Thus the mechanism that provides the force to deliver the medicament in self-injectors and autoinjectors is also used to extend the needle and the drug container to cause the insertion of the needle through the user's skin. The autoinjectors manufactured, for example by Owen Mumford, thus use very low pressures to inject the medicament, which is injected through a needle in a relatively slow stream. The pressures applied in the medicament-containing compartments of this type of device are very low, reaching a maximum of around 60 p.s.i. and take around 6 seconds to inject 1 mL. These devices do not deliver of the medicament using jet injection, so the medicament is delivered in a bolus at the tip the needle, which typically penetrates the patient by typically at least about 12 mm. When these low pressures and injection rates are used with shorter needles, especially those that penetrate the patient around 5 mm or less, there is a high incidence of leakback of the injected medicament around the needle or through the hole in the tissue created.

Prefilled syringes, such as those presently sold by Becton and Dickinson as the BD Hypak™ are intended for slow speed, manual or autoinjector injections. While prefilled syringes are readily available, the manufacturing techniques employed result in dimensional tolerances that traditionally have been considered too loose for jet injectors since the syringe would need to withstand a very sharp application of an elevated pressures sufficient to jet inject the medicament. Additionally, prefilled syringes include portions shaped to hold the needle and flanges for grasping for injection by hand that result in features that can be susceptible to breakage. Residual stresses that are present in the syringe bodies also increase their fragility, which is one of the reasons they have typically been considered too fragile for use in a jet injector. Thus, jet injectors have typically used more robust cartridges without features intended for handheld use, and which are manufactured with tighter tolerances than typical prefilled syringes.

An injector is needed that can reliable inject medicament to a desired site without a substantial risk of the medicament leaking back out from the patient's skin, at a fast speed substantially without regard to tissue resistance, and preferably being able to use a standard prefilled syringe.

SUMMARY OF THE INVENTION

The invention is related to a jet injector. The preferred embodiment employs a prefilled syringe that is preferably prefilled with a medicament prior to the assembly of the device. The syringe has a container portion that defines a fluid chamber containing a medicament. An injection-assisting needle is disposed at the distal end of the chamber and has an injecting tip configured for piercing an insertion location. The needle defines a fluid pathway in fluid communication with the chamber for injecting the fluid from the chamber into an injection site. The syringe also has a plunger that is movable within the fluid chamber.

In this embodiment, a housing houses the prefilled syringe and is configured for allowing insertion of the needle at the injection location to an insertion point that is at a penetration depth below the surface at the insertion location. A syringe support supportively mounts the prefilled syringe to the housing, and an energy source is configured to bias the plunger with a force selected to produce an injecting pressure in the medicament in the fluid chamber of between about 80 and 1000 p.s.i. This pressure injects the medicament from the fluid chamber through the needle to an injection site that is remote from the injecting tip. The penetration depth and injecting pressure are preferably sufficient to permit better medicament distribution than in autoinjectors and to substantially prevent backflow of the injected medicament. In the preferred embodiment, the injection rate is substantially unaffected by tissue resistance.

The energy source, which preferably comprises a spring, is preferably configured to produce the injecting pressure that remains below about 500 p.s.i. and above about 90 p.s.i. during the injection of the medicament. More preferably, the injecting pressure remains at least at about 100 p.s.i. and up to about 350 p.s.i. during the injection of the medicament.

The preferred housing is configured for allowing insertion of a portion of the needle to the penetration depth of between about 0.5 mm and 5 mm below the surface at the insertion location. In one embodiment, the penetration depth is between about 1 mm and 4 mm, and more preferably is less than about 3 mm. The injecting pressure and penetration depth in some embodiments preferably are sufficient such that the injection site is subcutaneous, although other types of injection can be achieved in other embodiments. For intramuscular injections, for example, the exposed portion of the needle can be around 10 mm to 15 mm, for example, with a preferred embodiment being around 13 mm.

The syringe has a distal portion of the prefilled syringe, in which the injection-assisting needle is located, and a proximal portion opposite the distal portion. The syringe support can be configured to axial support the proximal portion of the pre-filled syringe during the jet injection of the medicament, such that the distal portion of the prefilled syringe is substantially unsupported in an axial direction.

The prefilled syringe is preferably made of blown glass, which can be formed on the injection-assisting needle, but is usually formed and adhered to the needle. Additionally, the preferred volume of the fluid chamber is about between 0.02 mL and 4 mL of the medicament.

The housing of the preferred embodiment comprises a retractable guard that is movable between a protecting position and an injecting position. In the protecting position, the needle is disposed within the guard, but in the injecting position, the tip of the needle is exposed for insertion to the insertion point. A trigger mechanism can be operably associated with the energy source for activating the energy source to jet inject the medicament. The trigger mechanism is preferably configured for activating the energy source after the retractable guard is retracted from the protecting position, and most preferably once it is retracted to the injecting position.

A syringe cushion can be provided in association with the syringe support and the prefilled syringe to compensate for shape irregularities of the pre-filled syringe and/or to cushion and provide shock absorption to the syringe during the device firing. In one embodiment, a ram that is biased by the spring against the plunger to produce the injecting pressure is provided with a bell portion on which the spring of the energy source is seated. The bell portion defines a hollow interior configured for receiving the prefilled syringe when the device is fired, such that the spring surrounds the prefilled syringe.

The present invention thus provides a jet injection device that offers better medicament distribution and can reliably use a shorter needle that low pressure, non-jet injectors. Also, the inventive jet injector can benefit from simplified manufacturing by using a prefilled syringe, which traditionally is used for slow injections.

DETAILED DESCRIPTION OF THE PREFERRED EMBODIMENTS

Figure 1:
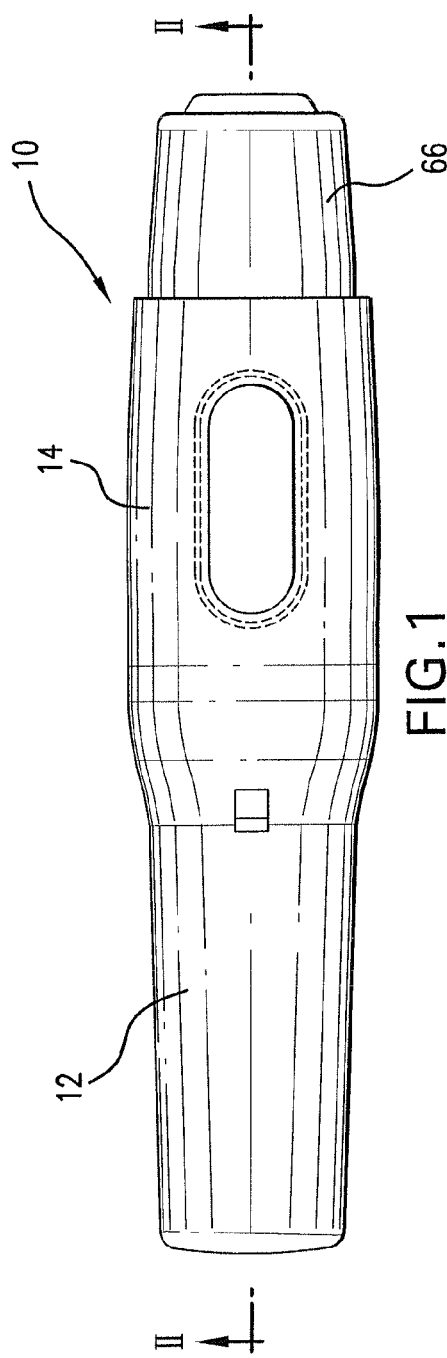
FIG. 1 is a side view of a preferred embodiment of a jet injector constructed according to the present invention, showing the injector prior to injection.
Figure 2:
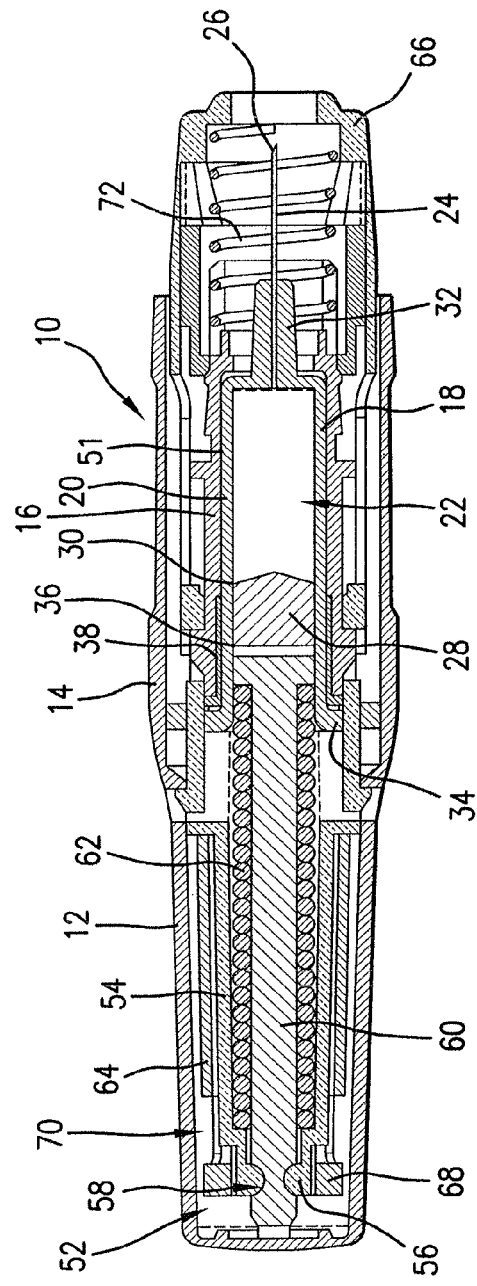
FIG. 2 is a cross-sectional view thereof taken along plane II-II.
Figure 3:
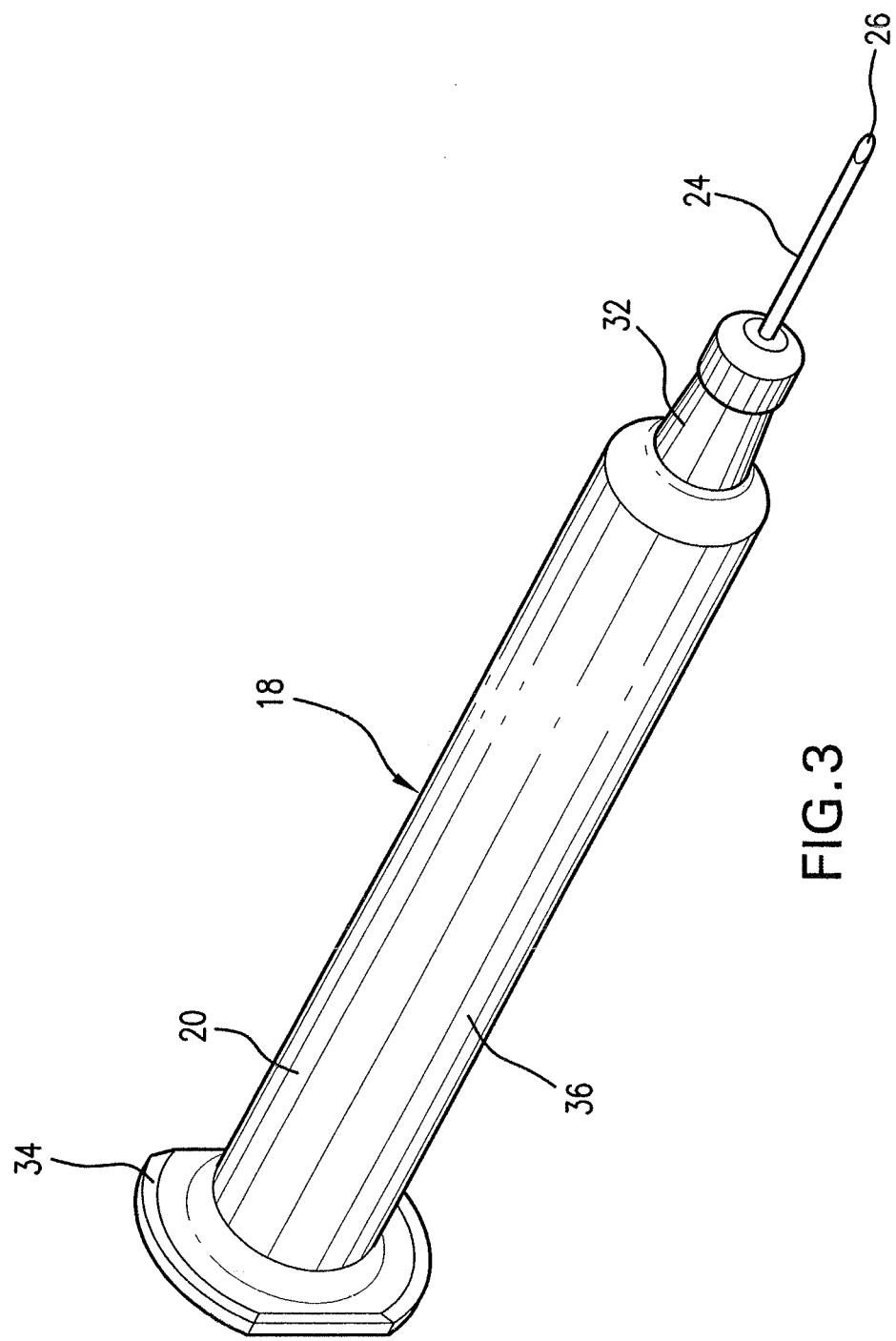
FIG. 3 is a perspective view of a prefilled syringe for use in the preferred embodiment

Referring to FIGS. 1 and 2, a preferred embodiment of an injector 10 has a housing 12 configured for allowing a user to handle the injector 10. The housing 12 includes an outer housing member 14 that substantially houses most of the components shown in FIG. 2. A syringe support member 16 is housed within and mounted with the housing 12. The syringe support member 16 is configured to hold and position a pre-filled syringe 18, which is shown in FIG. 3. In the preferred embodiment, the syringe support member 16 is substantially fixed to the housing 12, such as by snaps, an adhesive, a weld, or another known attachment. The prefilled syringe 18 has a container portion 20 that defines in its interior a fluid chamber 22, which is prefilled with medicament to be injected. At the distal end of the prefilled syringe 18 is an injection-assisting needle 24. Needle 24 has an injecting tip 26 configured as known in the art to penetrate the tissue of a patient, preferably the skin. A needle bore extends through the needle 24, as known of the art. The bore is in fluid communication with the medicament in the fluid chamber 22 and is open at the needle tip 26 to inject the medicament.

At a proximal side of the fluid chamber 22, opposite from the needle 24, is a plunger 28 that seals the medicament in the fluid chamber 22. A syringe wall 30 preferably comprises a tubular portion, preferably closed at a distal end and open at a proximal end, to define the fluid chamber 22. Plunger 28 is slideably received in the tubular portion. The prefilled syringe 20 is configured such that when the plunger 28 is displaced in a distal direction, the volume of the fluid chamber 22 is decreased, forcing the medicament out therefrom and through the bore of needle 24.

At the distal end of the fluid chamber 22 is a needle hub portion 32 to which the needle is mounted. A syringe flange 34 extends radially, preferably from the proximal end of the syringe wall 30.

In the preferred embodiment, the syringe 18 has a syringe body 36 that includes the flange 34 wall 30 and hub portion 32 is of unitary construction. A preferred material for the syringe body 36 is glass, but other materials can be used in other embodiments. A suitable prefilled syringe is the BD Hypak™, which is available in various sizes and volumes and is sold prefilled with medicament. The glass of the syringe body is adhered to the needle. Typical medicaments and medicament categories include epinephrine, atropine, sumatriptan, antibiotics, antidepressants, and anticoagulants. Using a prefilled syringe facilitates handling of the medicament when the injector is assembled, and there is an extensive body of knowledge of how the medicaments keep and behave in a prefilled syringe.

Figure 4:
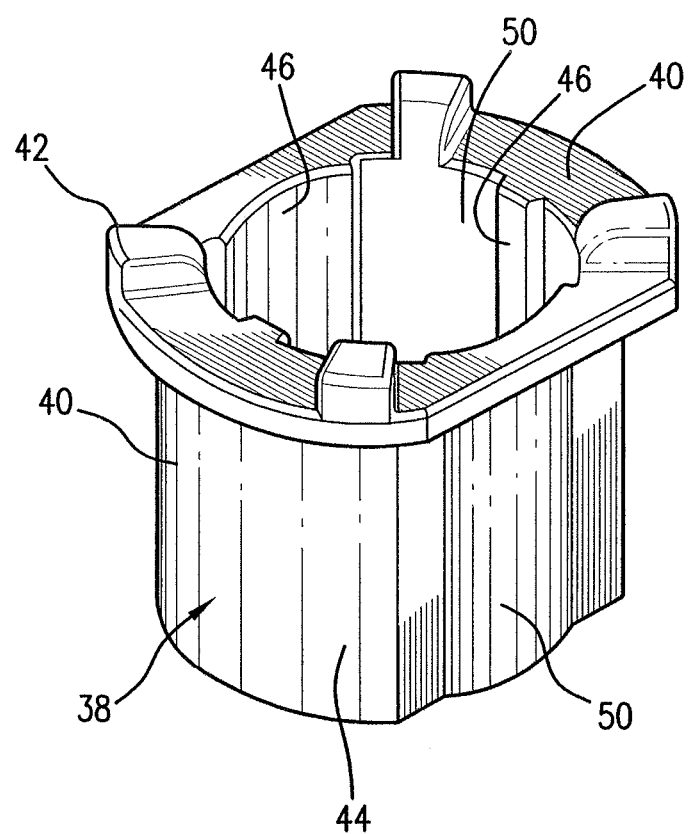
FIG. 4 is a perspective view of a syringe cushion of the preferred embodiment.

A syringe cushion 38, which is shown in detail in FIG. 4, is preferably made of an elastomeric material or other resilient material. A flange 40 of the syringe cushion 38 extends radially and is disposed and serves as an interface between the distal side of the syringe support member 16 and the syringe flange 34. Elevated portions, such as nubs 42 extend proximately from the cushion flange 40 and are configured and dimensioned to abut the syringe flange 34.

Prefilled syringes that are manufactured by a blown glass process can have significant dimensional tolerances and unevenness, particularly in the glass body 36. The cushion 38 can serve to accommodate the shape irregularities and to properly position and locate the prefilled syringe 18 within the syringe support 16. Typically, the axial thickness of glass blown syringe flanges on a 1 mL prefilled syringe is within about ±0.5 mm. For a BD Hypak™ 1 mL standard prefilled syringe, the thickness of the syringe flange 34 is 2 mm+0.5 mm or −0.4 mm, and in a 1 mL long configuration BD Hypak™ syringe, the flange axial thickness is about 1.65 mm±0.25 mm. Other dimensional variations that occur in typical glass prefilled syringes are in the internal and external diameters of the tubular wall 30. These variations can be accommodated by the resilient sleeve portion 44 of the syringe cushion 38, which extends axially around the interior of the syringe support 16. The syringe cushion 38 is preferably received in the interior of the syringe support member and receives the syringe body 36, preferably fitting snugly therein.

The sleeve portion 44 preferably has radially inwardly extending protrusions 46 with a surface area and configuration selected to allow the insertion of the prefilled syringe 18 therein during assembly, but providing sufficient friction to maintain the syringe 18 in place and to provide cushioning and shock absorption during the firing of the injector. Outward protrusions 48 are also provided on the sleeve portion 44, which can be received in corresponding recesses of the syringe support 16 to prevent axial rotation therebetween. Recessed areas 50 can be provided on the interior and exterior of the syringe cushion 38 opposite corresponding protrusions 48 on the opposite radial side of the sleeve portion 44 if an increased wall thickness of the sleeve portion 44 is not desired. In an alternative embodiment one or both of the flange 40 and sleeve 44 of the syringe cushion 38 are substantially smooth, substantially without any protrusions. Preferably, the material and configuration of the syringe cushion 38 is also sufficient to entirely support the prefilled syringe 20 to withstand a firing force applied axially in a distal direction on the plunger 28. Thus, the entire support for the prefilled 20 can be provided on the syringe flange 34, while the distal end of the syringe 18 may itself be substantially unsupported in an axial direction. This can help withstand the shock on the glass body 36 of the prefilled syringe 20 produced by the elevated pressures within the fluid chamber 22.

To radially position the distal end of the prefilled syringe 18, the syringe support 16 preferably has a narrowed bore portion 51 that is preferably configured to abut the outside of the syringe wall 30. This is especially beneficial when the needle is inserted into the patient's skin. The narrowed bore portion can be made of a resilient material, such as an elastomer, or it can be made unitarily with the rest of the syringe support 16, preferably of a plastic material.

A trigger mechanism 52 is preferably also housed within housing 12. The trigger mechanism 52 includes an inner housing 54 that can be attached to the outer housing 14, such as by snaps, an adhesive, a weld, or other known attachment. Trigger protrusions 56 extend inwardly from the proximal end of the inner housing 54 and are resiliently biased outwardly. Trigger protrusions 56 are received in a recess 58 of ram 60 in blocking association therewith to prevent distal movement of the ram 60 prior to the firing of the device. The ram 60 is urged towards the distal end of the injector 10 by an energy source, which preferably is a compression spring 52, although other suitable energy sources can alternative be used such as elastomer or compressed-gas springs. A preferred type of compression spring is a coil spring.

A trigger member of the trigger mechanism 52, such as a latch housing 64, is provided exterior to the inner housing to retain the trigger protrusions 56 in the blocking association in the recess 58 to prevent premature firing of the injector 10. The latch housing 64 is slideable inside the outer housing 14 with respect to the inner housing 54, preferably in an axial direction, and the latch housing 64 preferably surrounds the inner housing 54.

Figure 5:
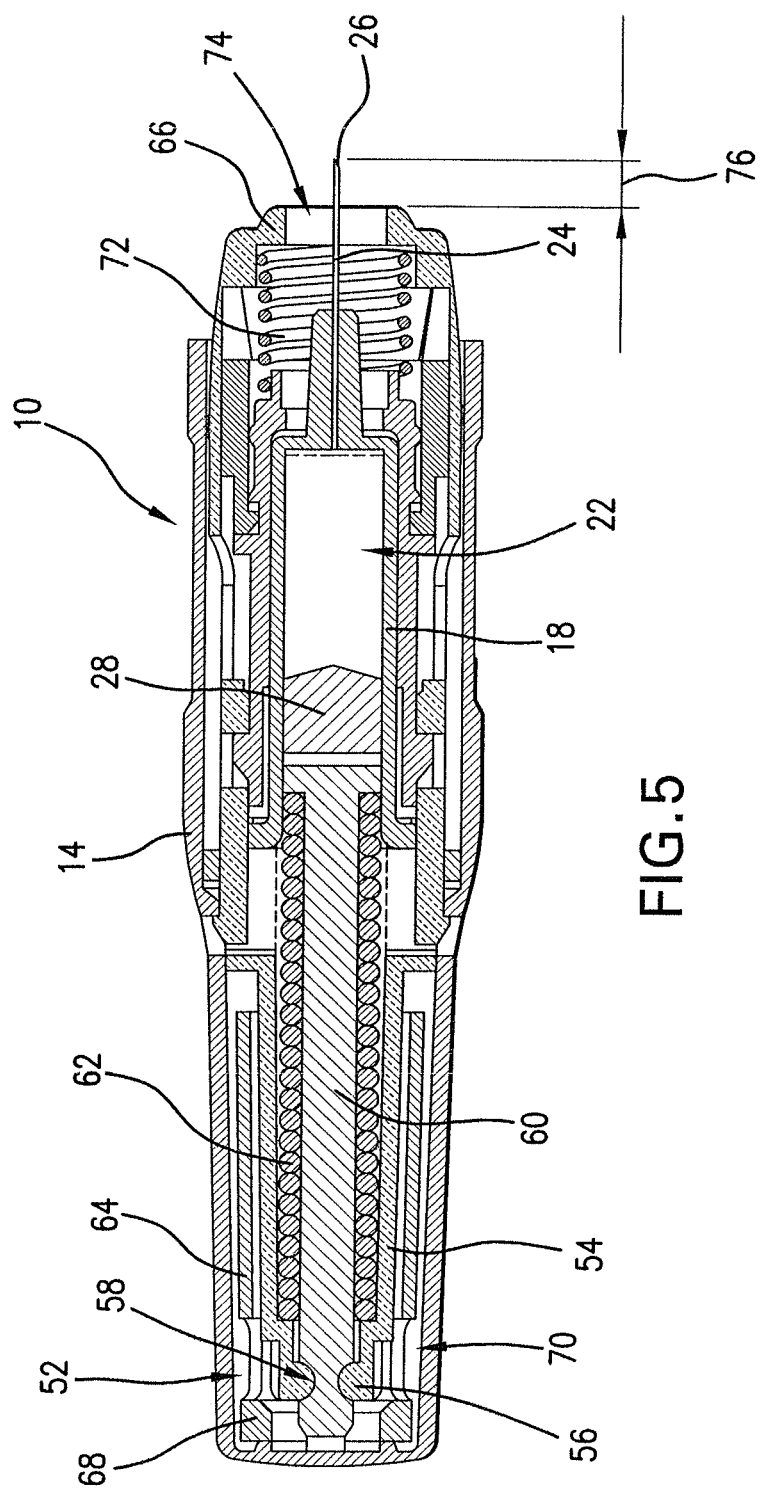
FIG. 5 is a cross-sectional view of embodiment of FIG. 1, showing the injector at the start of the jet injection of the embodiment contained therein.

The housing 12 has a needle guard 66 that is moveable with respect to the outer housing 14. The needle guard 66 is shown in FIGS. 1 and 2 in a protecting position, in which the needle 24 is disposed within the guard 66. The needle guard 66 is retractable, preferably into the out housing 14, in a proximal direction to an injecting position, in which the needle tip 26 and an end portion of the needle 24 is exposed as shown in FIG. 5 for insertion into a patient. In the preferred embodiment, the proximal movement of the guard is prevented substantially at the injecting position.

The needle guard 66 is associated with the latch housing 64 such that when the guard 66 is displaced distally it slides the latch housing 64 also in a distal direction to release the trigger protrusions 56 from the recess 58. Preferably, the latch housing 64 has a latching portion 68 that abuts the inner housing 54 in an association to bias and maintain the trigger protrusions 58 positioned in the blocking association with the ram 60 prior to the firing of the device 10. When the latch is slid proximately by the retracting of the guard 66 to the injecting position, the latching portion 68 slides beyond the portion of inner housing 54 that is contacts to flex the trigger protrusions 56 into the recess 58 of the ram 60, allowing the trigger protrusions 56 to move radially outwardly from the recess 58 and therefore from the blocking association. When this happens, spring 62 biases the ram 60 against plunger 28 to fire the jet injector. Latch housing 64 preferably defines trigger openings 70 adjacent to latching portions 68, which is configured to receive a portion of the inner housing 54, such as the surface disposed radially outwardly from the trigger protrusions 56.

The guard 66 is preferably resiliently biased distally towards the protecting position by compression coil spring 72. Also, the needle guard 66 has an axial opening 74 to allow the needle 24 pass there through, and which may be sized according to the type of injector desired. The construction of the present embodiment allows a user to push the distal end of the injector 10 against the patient's skin, pushing the needle 24 into the skin at an insertion location, substantially at the same speed as the injector is pushed. Once the needle 24 is fully inserted to an insertion point at a penetration depth, the trigger mechanism 56 fires the jet injection to an injection site.

Preferably, the prefilled syringe 18 and its needle 24 are not shuttled forward automatically into the patient's skin, such as by the firing energy source during the injection firing. The user preferably gently pushes the entire device forward to insert the needle, preferably retracting a guard against the skin in the process. The prefilled syringe 18 preferably remains is a substantially stationary within the housing 12, and is preferably substantially fixed thereto. In this manner, the present invention provides for a gentler treatment of the syringe during injection that enables the use of a sufficiently powerful spring 62 or other energy source to produce a jet injection without the risk of damaging the relatively fragile and complex shapes of the prefilled syringe, also allowing, for example, the injection of high viscosity solutions, where the risk of breaking a syringe, such as at the flange, is elevated in prior art injectors that shuttle the syringe forward in the housing and into the patient. Residual stresses are also often present in the glass bodies of prefilled syringes, and this configuration reduces the additional stresses imposed thereon during use, further protecting the syringe. Also, misalignments in the prefilled syringe are also rendered operationally less significant due to the gentle insertion of the needle that is possible with this configuration.

Preferably, the injecting position of the guard 66 is such that a predetermined length of the end of needle 24 is exposed from the guard 66. In some embodiments, such as where the opening 74 is of a sufficiently large diameter, the skin of the patient maybe allowed to extend into the opening 74 when the device 10 is pressed there against, and a needle that does not protrude beyond the distal end of the guard 66 can be used while still penetrating the skin to a certain depth. In most embodiments, the distance 76 by which the needle tip 26 extends past the distal end of the guard 66 will be fairly close to the depth of the insertion of the needle.

In the preferred embodiment, such as for subcutaneous injection, the guard 66 is configured to allow insertion of the needle to a penetration depth in the skin that is up to about 5 mm below the skin surface. More preferably, the penetration depth is less than about 4 mm, and in one embodiment is less than about 3 mm. Preferably, the insertion depth is at least about 0.5 mm and more preferably at least about 1 mm. In another embodiment, the distance 76 by which the needle extends past the guard 66 or the distal surface of the guard 66 that contacts the skin is up to about 5 mm, more preferably up to about 4 mm, and in one embodiment up to about 3 mm. Preferably, extension distance 76 is at least about 0.5 mm, more preferably at least about 1 mm, and most preferably at least about 2 mm. In a preferred embodiment, tip 26 extends by a distance 76 of around 2.5 mm beyond the portion of the guard 66 that contacts the skin in the injecting position.

In another embodiment, such as for intramuscular injection, the injector is configured to allow the needle to be inserted into the patient to a penetration depth in the skin, or alternatively beyond the distal surface of the guard, by a distance of up to about 15 mm. In one embodiment, this distance is about between 10 mm and 14 mm. In an embodiment for jet injection of epinephrine for instance, a preferred penetration depth or distance beyond the guard is between about 12 mm and 13.5 mm, and most preferably around 12.7 mm. Jet injection with this length needle improves the distribution of the medicament in the patient tissue compared to non jet injection. Other exposed needle lengths can be selected for jet injection to different depths below the skin, with a preferred overall penetration length of between about 0.5 mm and about 20 mm. In these embodiments, the needle guard is preferably configured for retracting from a protecting position, preferably covering the entire needle, to an injecting position, in which the desired length of the end of the needle is exposed.

The spring 62 and the prefilled syringe 18 are configured to jet inject the medicament. Thus, the spring 62 applies a force on the plunger 28 that is sufficient to elevate the pressure within the fluid chamber 22 to a level high enough to eject the medicament from the needle 24 as a jet. Jet injection is to be understood as an injection with sufficient velocity and force to drive the medicament to locations remote from the needle tip 26. In manual and autoinjector-type injections, in which the injection pressures are very low, the medicament exits the needle tip inside the patient and is typically deposited locally around the needle in a bolus. On the other hand, with the present jet injection device 10, the medicament is jet injected distally or in other directions, such as generally radially by the elevated pressure jet, which beneficially improves the distribution of the medicament after the injection and keeps a large bolus from forming that can detrimentally force the medicament to leak back out of the patient around the needle or through the hole left behind by the needle after it is removed.

Figure 6:
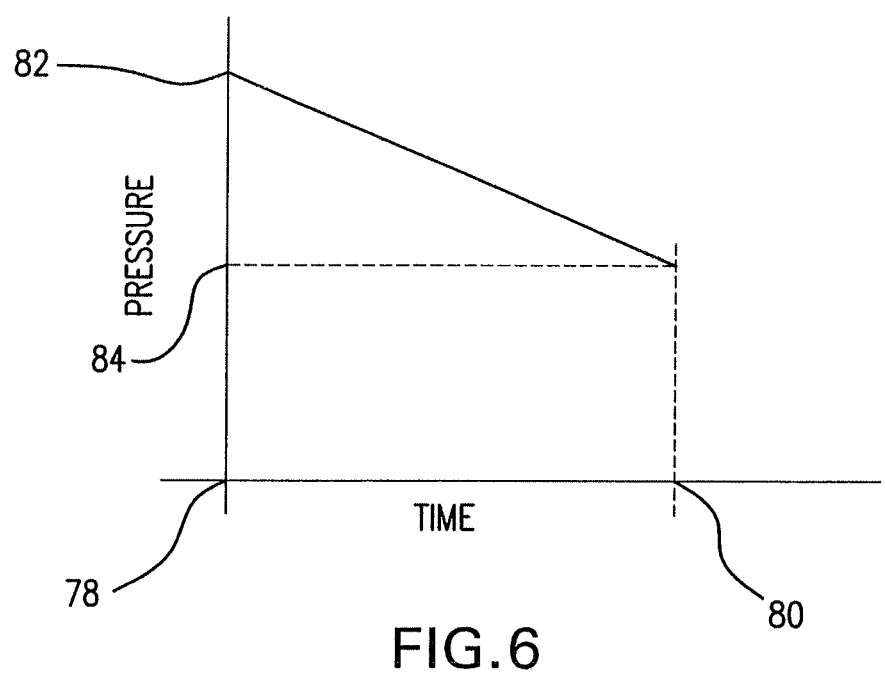
FIG. 6 is a graph showing the typical pressure present in the polluted chamber that contains medicament in the preferred embodiments during jet injection.

Referring to the graph shown in FIG. 6, numeral 78 represents the point in time when device 10 is fired, and numeral 80 represents the point of completion of the medicament injection, preferably when the plunger 28 hits the forward wall of the container portion 20. Numeral 82 represents the initial and peak pressure during the injection, and numeral 84 represents the final and low pressure during the injection. Since the spring 62 of the preferred embodiment has a linear spring constant and an injection-assisting needle is used to puncture the skin before commencing the injection, the pressure drops substantially linearly from the start of the injection 78 until the injection is completed. The final pressure 84 at the end 80 of the injection is sufficiently elevated so that even at the end of the firing stroke of ram 60, the medicament is still jet injected, and a very small amount or none of the medicament is deposited in a bolus around the needle tip 26.

Preferably the peak pressure during the injection is less than about 1,000 p.s.i., more preferably less than 500 p.s.i., and most preferably less than about 350 p.s.i. At the end 80 of the injection, the pressure 84 applied to the medicament in the fluid chamber 22 is preferably at least about 80 p.s.i., more preferably at least about 90 p.s.i., and most preferably at least about 100 p.s.i. In one embodiment of the invention, the initial pressure 82 is around 330 p.s.i., and the final pressure is about 180 p.s.i., while in another embodiment the initial pressure 82 is about 300 p.s.i., dropping to around 110 p.s.i. at the end 80 of the injection. The needles used in these embodiments are between 26 and 28 gage, and are most preferably around 27 gage, but alternatively other needle gages can be used where the other components are cooperatively configured to produce the desired injection. Preferably, the components of the injector 10 are configured to jet inject the medicament to a subterranean injection site.

The amount of medicament contained and injected from fluid chamber 22 is preferably between about 0.02 mL and 4 mL, and preferably less than about 3 mL, and in the preferred embodiment is around 1 mL. Larger volumes may also be selected depending on the particular medicament and dosage required. Preferably, the prefilled syringe is assembled into the remaining parts of the jet injector 10 already containing the desired amount of medicament. In a preferred embodiment, the prefilled syringe contains about 1 mL of medicament.

Preferred injection rates are below about 0.75 mL/sec., more preferably below about 0.6 mL/sec., and preferably at least about 0.2 mL/sec., more preferably at least about 0.3 mL/sec, and most preferably at least about 0.4 mL/sec. Preferably, the injection of the entire amount of medicament is completed in less than about 4 seconds, more preferably in less than about 3 seconds, and most preferably in less than about 2.5 seconds. Preferably, the medicament injection takes at least about 1 second, and more preferably at least 1.5 seconds, and most preferably at least about 1.75 seconds. A preferred embodiment injects the medicament at about 0.5 mL/sec., completing the injection of 1 mL in about 2 seconds.

U.S. Pat. No. 6,391,003 discloses several experimental results of pressures that can be applied to medicament in a glass cartridge, using 26 and 27 gage needles. The following table illustrates injections with different peak pressures that can be used with glass prefilled syringes:

| Pressure and Time (sec.) to Inject 1 cc | | |
| --- | --- | --- |
| Pressure | 26 Gauge needle | 27 Gauge needle |
| 150 p.s.i. | 2.1 | 4.2 |
| 200 p.s.i. | 1.9 | 3.9 |
| 240 p.s.i. | 1.7 | 3.3 |
| 375 p.s.i. | 1.4 | 3.1 |

It is foreseen that higher pressures and flow rates will be used with shorter needle penetration into the patient skin to achieve jet injections to a particular desired depth substantially without medicament leakback.

It has been found that using the jet injection of the present device, short needles can be used to inject medicament to different parts of the skin, preferably subcutaneously, substantially without any leakback. Using a needle that extends by about 2.5 mm from the needle guard 66, a 27 gauge needle 24, and a pressure in the fluid chamber 22 peaking at around 300 p.s.i. and ending at around 100 p.s.i., resulting in a flow rate of about 0.5 mL/sec., 1 mL of medicament has been found to successfully be injected without leakback in close to 100% of the tested injections. Thus, the needle-assisted jet injector of the present invention permits jet injection of the medicament using a very short needle reliably regardless of the thickness of the patient's skin or the patient's age, weight or other typical factors that complicate non-jet injecting with short needles.

Figure 7:
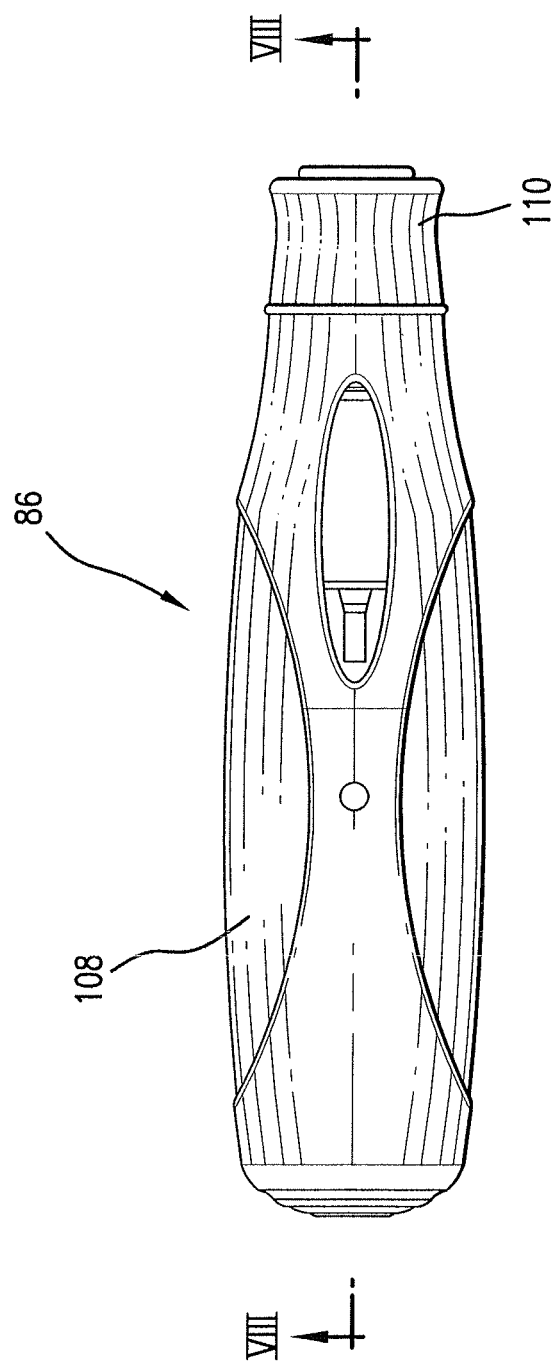
FIG. 7 is a side view of another embodiment of an injector that is configured for using a narrow diameter prefilled syringe.
Figure 8:
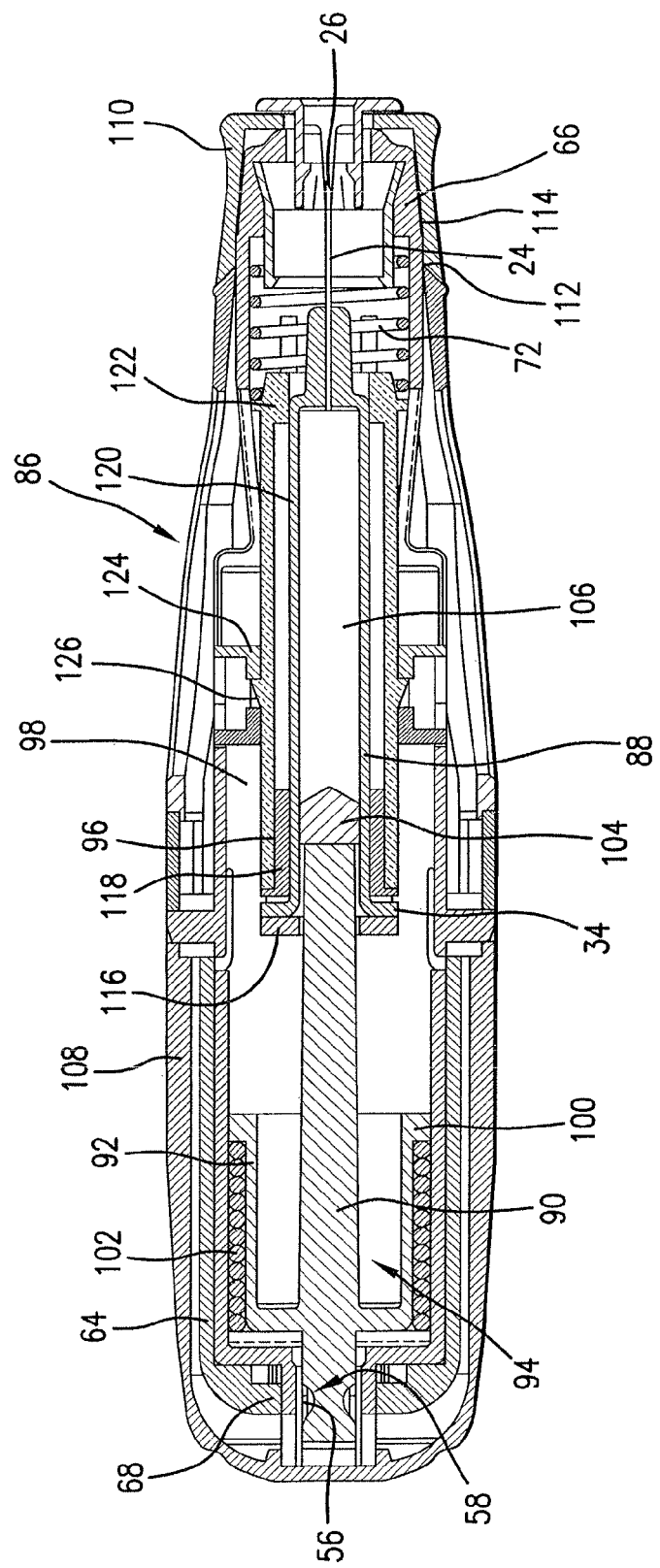
FIG. 8 is a cross-sectional view thereof; taken on VIII-VIII.

FIGS. 7 and 8 show another embodiment of the present invention that uses a prefilled syringe that has a long, but smaller-diameter configuration than the embodiment of FIG. 2. While in the embodiment of FIG. 2, the firing spring 62 extends into the bore of the prefilled syringe 18 during the firing stroke, the narrower prefilled syringe 88 of injector 86 does not provide as much space to accommodate a spring. Consequently, the ram 90 of injector 86 includes a bell portion 92 defining a hollow interior 94 that is configured to receive the proximal end of the prefilled syringe 88 and the syringe support 96 when the injector 86 is fired. Similarly, a bell-receiving space 98 is defined around the exterior of the prefilled syringe 88 and syringe support 96 to receive the bell portion 92 during the firing. The bell 92 includes a spring seat 100 extending radially outwardly and configured and disposed to seat a compression spring 102. When the trigger mechanism 56 is activated and the device 86 is fired, spring 102 acts against seat 100 to drive the ram 90 against plunger 104 to jet inject the medicament from the fluid chamber 106. As a result, after firing, the spring 102 radially surrounds the prefilled syringe 88. The outer housing portion 108 is wider than outer housing portion 14 of injector 10 to accommodate the bell portion 92 and larger diameter spring 102.

One available long configuration syringe with a 1 mL capacity has a cylindrical syringe body portion with a diameter of 8.15 mm, which would typically be used in the injector of FIGS. 7 and 8, while one available shorter configuration syringe of the same capacity has a cylindrical syringe body portion with a diameter of 10.85 mm, which would be used in the injector of FIGS. 1 and 2. While the embodiment with a bell portion can be used with wider/shorter syringes, I is preferred with prefilled syringes having an outer diameter cylindrical wall of less than about 10 mm, and more preferably of less than about 9 mm.

Injector 86 also includes a cap 110 fitted around the needle guard 66, and associated with the outer housing 108 to prevent retraction of the needle guard 66 and the triggering of the device 86. Additionally, the cap 110 seals off the needle tip 26 and can be removed prior to using the device 86. The cap 110 is preferably configured to fit over the needle guard 66 in a snap-fit association therewith, such as by including a narrower diameter portion 112 associated with an enlarged diameter portion 114 of the needle guard 66.

Additionally, injector 86 employs a syringe cushion cap 116 that extends around the outside of the syringe flange 34 from the syringe cushion 118 to help trap and retain the prefilled syringe 88. A cushion cap 122 is connected to the cushion 118 and is preferably of unitary construction therewith. The cushion cap 122 abuts the distal end of the syringe body 120 to radially position and hold the proximal end of the body 120 while the needle 24 is being inserted into the patient. Similarly to the embodiment of FIG. 2, the syringe holder 96 is associated with the housing in a substantially fixed position, such as by mounting portion 124, which traps protrusions 126 of the syringe holder.

Figure 9:
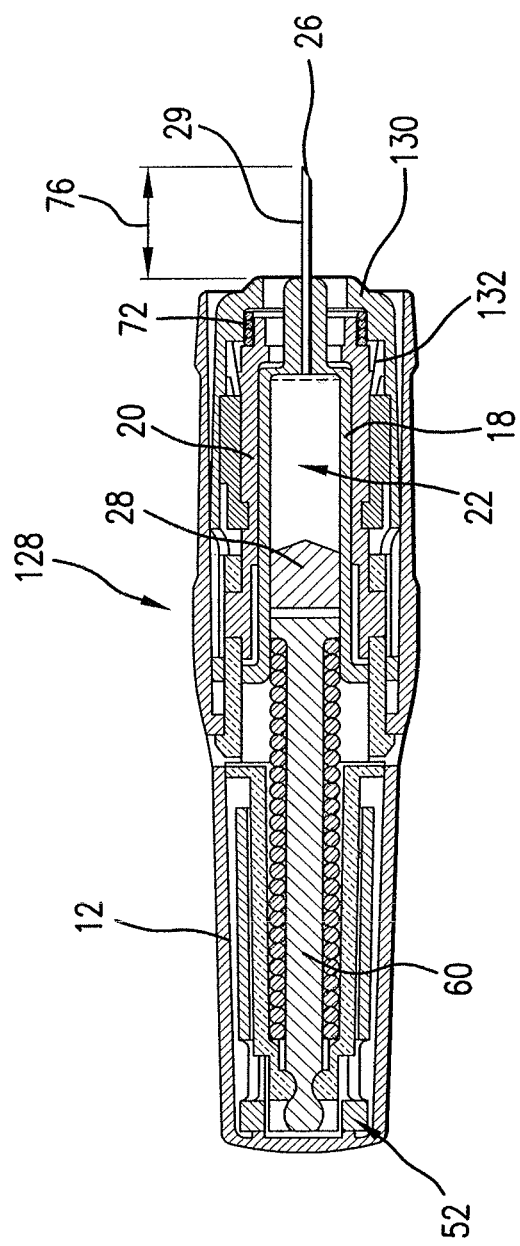
FIG. 9 is a cross-sectional view of another embodiment of an injector using a needle for intramuscular jet-injection.

Referring to FIG. 9, injector 128 has a needle guard 130 configured to retract further into the injector housing than the injector of FIGS. 1 and 2 or FIG. 5 before the trigger mechanism 52 fires the jet injection. The injector in this figure is shown in a position in which the trigger mechanism 52 is being released and about to fire the injection. The distance 76 by which the needle extends past the guard 130 or the distal surface of the guard 130 that contacts the skin preferably between about 12.5 and 13 mm. In the preferred embodiments, the guard is preferably configured to reextend to a protecting position after the device is fired and removed from the patient, such as under the bias of spring 72, and is locked in that position by locking members 132, as known in the art to prevent reuse on the injector.

In other embodiments, the guard length, the location of the guard injecting position with respect to the needle tip (including the guard throw between the protecting and injecting positions), and the length of the needle from the syringe body can be selected to allow for shallower or deeper needle insertions before the device is fired, providing lesser or greater distances 76, respectively. Preferably, the guard is kept from sliding further back than substantially at the firing position, to better control in insertion depth into the patient.

The entire disclosure of U.S. Pat. No. 6,391,003 is hereby incorporated herein by reference thereto.

While illustrative embodiments of the invention are disclosed herein, it will be appreciated that' numerous modifications and other embodiments may be devised by those skilled in the art. For example, the features for the various embodiments can be used in other embodiments, such as the needle and guard cap of FIGS. 7 and 8, which can be applied to the embodiment of FIG. 1. Therefore, it will be understood that the appended claims are intended to cover all such modifications and embodiments that come within the spirit and scope of the present invention.

What is claimed is:

1. A jet injector, comprising: a syringe support configured for supporting a syringe by a radial flange thereof, which syringe comprises: a syringe body that includes: a syringe wall defining a container portion defining a fluid chamber containing a medicament, a flange extending radially from the syringe wall and shaped for grasping for injection by hand when the syringe is used independently, and a plunger movable within the fluid chamber to expel the medicament, and a needle disposed at the distal end of the syringe body, having an injection tip configured for piercing an insertion location, and defining a fluid pathway in fluid communication with the chamber for injecting the fluid expelled from the chamber into an injection site; an energy source configured for biasing the plunger with a force sufficient to produce an injecting pressure in the medicament in the chamber maintained between about 80 p.s.i. and 1000 p.s.i, during injection of the medicament to jet inject the medicament from the fluid chamber through the needle to the injection site; and a cushion associated with the syringe support and made of a sufficiently resilient material and configured to compensate for shape irregularities of the flange and absorb shock on the flange from the jet injection to protect the flange from breaking.

2. The jet injector of claim 1, wherein the flange extends from a proximal portion of the syringe wall.

3. The jet injector of claim 2, wherein the injector is configured for supporting the syringe body during the jet injection only from the proximal portion of the body, such that the distal portion of the body is substantially unsupported axially.

4. The jet injector of claim 2, wherein the injector is configured for supporting the syringe body substantially only from the flange during the jet injection, by the support and cushion, such that the distal portion of the body is substantially unsupported axially.

5. The jet injector of claim 2, wherein the support and cushion are configured for supporting substantially only the flange during the jet injection, such that the distal portion of the body is substantially unsupported axially.

6. The jet injector of claim 5, wherein the flange is of unitary construction with the body, which are made of glass.

7. The jet injector of claim 6, wherein the body further comprises a needle hub of unitary construction with the wall, the needle hub being adhered to the needle.

8. The jet injector of claim 2, wherein the support and cushion are configured for entirely supporting the syringe from the flange during the jet injection, such that the distal portion of the body is substantially unsupported axially.

9. The jet injector of claim 1, wherein the syringe support comprises a sleeve configured for receiving the wall axially therein, and the cushion has flange portion extending radially and disposed to interface axially between the flange and the sleeve for compensating for the shape irregularities and absorbing the shock from the injection.

10. The jet injector of claim 9, wherein the syringe body is made of blown glass.

11. The jet injector of claim 1, wherein the cushion comprises axially elevated portions of the resilient material configured for abutting the syringe flange.

12. The jet injector of claim 1, wherein the resilient material is an elastomeric material.

13. The jet injector of claim 1, wherein support is configured for supporting a prefilled syringe dimensioned such that the energy source produces the jet injection, using the needle as an injection-assisting needle.

14. The jet injector of claim 1, wherein the energy source and prefilled syringe are configured such that the injecting pressure remains above about 90 p.s.i. and below about 500 p.s.i. during the injection of the medicament.

15. The jet injector of claim 1, wherein the energy source is configured to produce the injecting pressure that remains between about 100 p.s.i. and 350 p.s.i. during the injection of the medicament.

16. The jet injector of claim 1, further comprising: a housing that houses the syringe support and cushion, wherein the housing is configured for allowing insertion of the needle to penetration depth, which is between about 0.5 mm and 5 mm below the surface at the insertion location; and a ram in driven association with the energy source for driving the plunger into the body to expel the medicament; wherein the energy source and ram are configured to produce the injecting pressure sufficient for ejecting the medicament with sufficient velocity for delivery remote from the penetration depth of the needle by jet injection.

17. The jet injector of claim 1, further comprising a housing portion that houses the syringe support, the cushion, and the energy source, wherein syringe support and cushion are associated for holding the syringe body in a fixed position before and during activation of the energy source for firing of the jet injector.

18. The jet injector of claim 17, further comprising: a retractable guard that is movable with respect to the housing portion between: a protecting position in which the needle is disposed within the guard, and an injecting position in which the tip of the needle is exposed for insertion to the insertion point; and a trigger mechanism operably associated with the guard and energy source for activating the energy source to jet inject the medicament upon retraction of the guard to the injecting position.

19. The jet injector of claim 1, wherein the energy source comprises a spring, and the jet injector further comprises a ram that is biased by the spring against the plunger for driving the plunger into the body to expel the medicament, wherein the ram comprises a bell portion on which the spring is seated, and the bell portion defines a hollow interior configured for receiving the prefilled syringe and syringe support when the device is fired, such that the spring surrounds the prefilled syringe after the firing.

20. The jet injector of claim 1, further comprising the syringe held by the syringe support and cushion.

21. A jet injector, comprising: a prefilled syringe, that comprises: syringe body of unitary construction made of glass, comprising: a syringe wall defining a container portion defining a fluid chamber containing a medicament, a flange extending radially from a proximal portion of the syringe wall and shaped for grasping for injection by hand when the syringe is used independently, and a plunger movable within the fluid chamber to expel the medicament, and a needle disposed at the distal end of the syringe body, having an injection tip configured for piercing an insertion location, and defining a fluid pathway in fluid communication with the chamber for injecting the fluid expelled from the chamber into an injection site; a syringe support supporting the syringe body by the flange; an energy source configured for biasing the plunger with a force sufficient to produce an injecting pressure in the medicament in the chamber maintained between about 80 p.s.i. and 1000 p.s.i. during injection of the medicament to jet inject the medicament from the fluid chamber through the needle to the injection site; and a cushion associated with the syringe support and made of a sufficiently resilient material and configured to compensate for shape irregularities of the prefilled syringe and absorb shock on the flange from the jet injection to protect the flange from breaking.

22. The jet injector of claim 21, wherein the support and cushion are configured for supporting substantially only the flange during the jet injection, such that the distal portion of the body is substantially unsupported axially.

23. The jet injector of claim 21, wherein the body further comprises a needle hub of unitary construction with the wall, the needle hub being adhered to the needle.

24. The jet injector of claim 21, wherein the syringe body is made of blown glass.

25. The jet injector of claim 22, wherein the resilient material is an elastomeric material.

26. The jet injector of claim 21, further comprising a housing portion that houses the syringe support, the cushion, the syringe, and the energy source, wherein syringe support and cushion hold the syringe body in a fixed position before and during activation of the energy source for firing of the jet injector.

27. The jet injector of claim 21, further comprising: a housing that houses the syringe support and cushion, wherein the housing is configured for allowing insertion of the needle to penetration depth, which is between about 0.5 mm and 5 mm below the surface at the insertion location; and a ram in driven association with the energy source for driving the plunger into the body to expel the medicament; wherein the energy source and ram are configured to produce the injecting pressure sufficient for ejecting the medicament with sufficient velocity for delivery remote from the penetration depth of the needle by jet injection, thereby using the needle as an injection-assisting needle.

28. The jet injector of claim 21, wherein the energy source is configured to maintain the injecting pressure between about 100 p.s.i. and 350 p.s.i. during the injection of the medicament.

* * * * *